United States Patent [19]
Yassinzadeh et al.

[11] Patent Number: 5,700,695
[45] Date of Patent: Dec. 23, 1997

[54] SAMPLE COLLECTION AND MANIPULATION METHOD

[75] Inventors: Zia Yassinzadeh, 11240 Mount Hamilton Rd., San Jose, Calif. 95140; Paul J. Lingane, Belmont, Calif.

[73] Assignee: Zia Yassinzadeh, San Jose, Calif.

[21] Appl. No.: 269,253

[22] Filed: Jun. 30, 1994

[51] Int. Cl.$^6$ ..................................................... G01N 1/10
[52] U.S. Cl. .......................... 436/180; 436/148; 436/169; 436/177; 73/863.11; 73/863.12; 73/864.52; 73/864.61; 422/99; 422/100; 422/101; 128/763; 128/764; 128/765
[58] Field of Search .................................... 128/763–765; 73/863.11, 863.12, 864.52, 864.61; 422/99–102; 436/148, 150, 177, 169, 180

[56] References Cited

U.S. PATENT DOCUMENTS

| | | | |
|---|---|---|---|
| 3,162,195 | 12/1964 | Dick | 128/764 |
| 3,468,635 | 9/1969 | Richmond | 436/155 X |
| 3,491,748 | 1/1970 | Pate | 128/766 |
| 3,640,267 | 2/1972 | Hurtig et al. | 128/765 |
| 3,682,596 | 8/1972 | Stone | 422/101 |
| 3,748,099 | 7/1973 | Horlach | 422/102 X |
| 3,748,909 | 7/1973 | Kuo | 422/100 X |
| 3,799,742 | 3/1974 | Coleman | 422/102 X |
| 3,901,765 | 8/1975 | Mehl | 435/34 |
| 3,965,889 | 6/1976 | Sachs | 422/101 X |
| 4,063,460 | 12/1977 | Svensson | 422/100 X |
| 4,088,448 | 5/1978 | Lilja et al. | 422/102 |
| 4,150,089 | 4/1979 | Linet | 422/102 |
| 4,195,524 | 4/1980 | Hansen | 73/863.11 |
| 4,215,702 | 8/1980 | Ayer | 128/766 |
| 4,326,541 | 4/1982 | Eckels | 128/766 |
| 4,537,747 | 8/1985 | Castaneda | 422/100 |
| 4,627,445 | 12/1986 | Garcia et al. | 128/770 |
| 4,637,403 | 1/1987 | Garcia et al. | 128/770 |
| 4,753,776 | 6/1988 | Hillman et al. | 422/101 |
| 4,812,293 | 3/1989 | McLaurin et al. | 422/101 X |
| 4,816,224 | 3/1989 | Vogel et al. | 422/55 |
| 4,865,813 | 9/1989 | Leon | 422/102 X |
| 4,933,092 | 6/1990 | Aunet et al. | 422/101 X |
| 5,090,420 | 2/1992 | Nielsen | 128/764 |
| 5,135,719 | 8/1992 | Hillman et al. | 422/101 |
| 5,232,667 | 8/1993 | Hieb et al. | 422/105 X |

FOREIGN PATENT DOCUMENTS

| | | | |
|---|---|---|---|
| 950588 | 9/1949 | France . | |
| 2269969 | 5/1974 | France . | |
| 913022 | 12/1962 | Germany . | |
| 369411 | 2/1973 | U.S.S.R. | 436/180 |
| 2211111 | 6/1989 | United Kingdom . | |

*Primary Examiner*—Arlen Soderquist
*Attorney, Agent, or Firm*—Townsend and Townsend and Crew LLP

[57] ABSTRACT

A sample collection and manipulation apparatus (2), typically used for collecting and manipulating a blood sample and measuring a component of that sample with the use of a reagent or ion-selective electrodes, includes a body member (4, 6, 8) defining a thermal pressure chamber (22) and a sample port (10). A measurement chamber (26) is formed along a fluid passageway (42, 16, 24) connecting the thermal pressure chamber with the sample port. The air within the thermal pressure chamber is preheated (54, 56, 60, 62, 63/65) to reduce its density and the sample port is then placed in contact with the liquid. As the gas cools, a partial vacuum is created within the thermal pressure chamber to draw a liquid sample through the passageway and into the measurement chamber. Appropriate analyte measurement techniques, such as optical or electrochemical, can then be carried out. Applications include the testing of blood gases, glucose, hemoglobin, electrolytes, coagulation and therapeutic drugs.

3 Claims, 6 Drawing Sheets

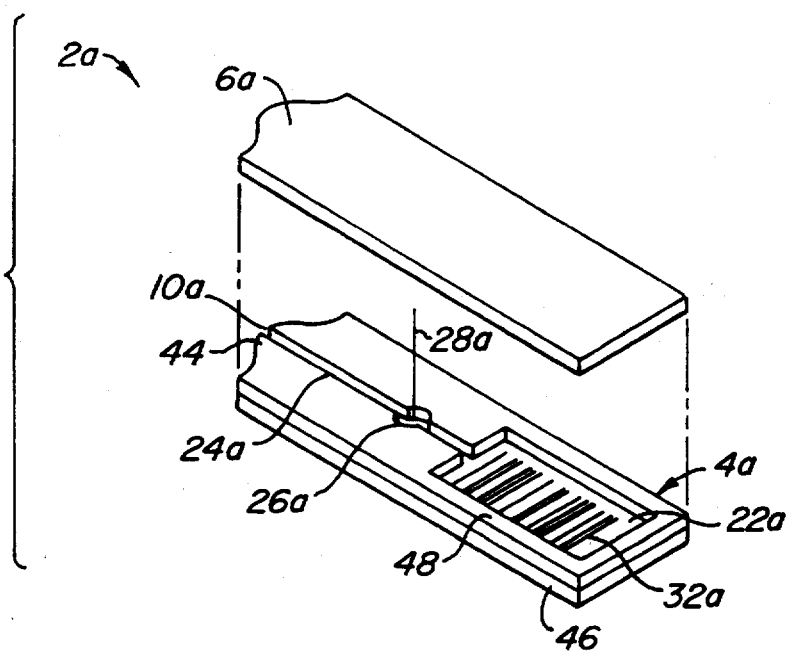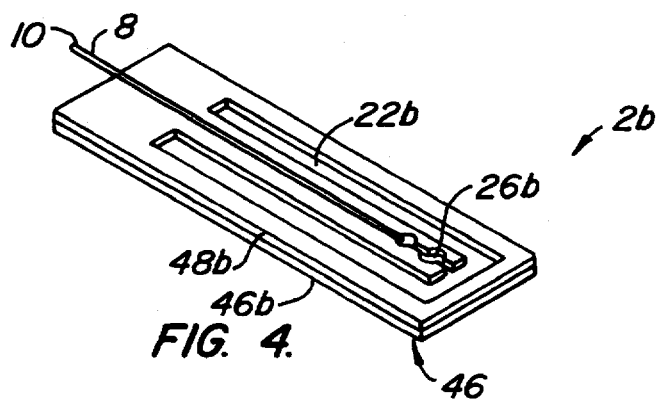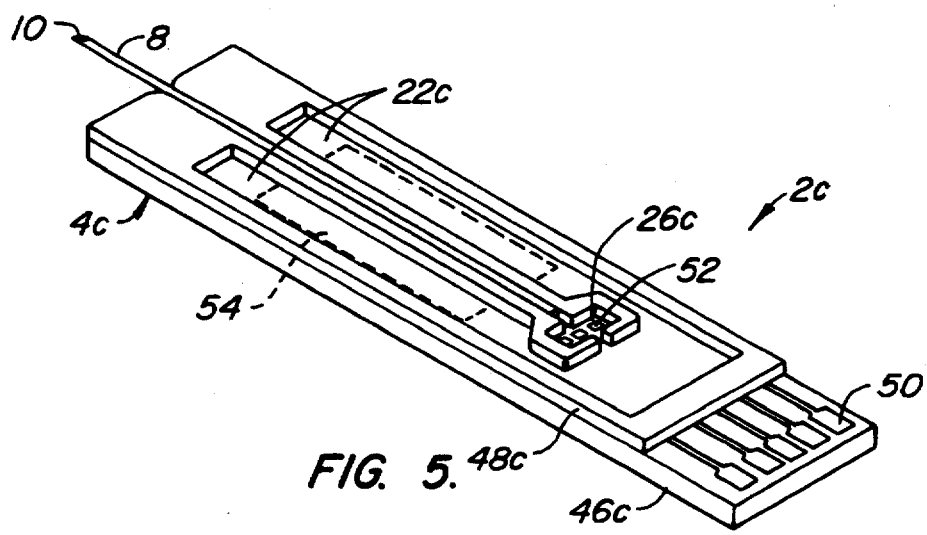

SAMPLE COLLECTION AND MANIPULATION METHOD

BACKGROUND OF THE INVENTION

Traditional medical lab tests for blood require that the sample be obtained by a syringe from a vein, transferred to a collection tube and then sent to a lab for analysis. Recently, methods for some tests have been developed that use only a drop of blood from a finger stick. A lancet is used to prick the finger which is then squeezed to obtain a 10–20 µl drop. The sample can be transferred by a capillary tube to a measuring device or the drop can be applied directly to a paper test strip or a small disposable plastic cuvette. Optical or other means of measurement on the blood in the cuvette can be made using an appropriate instrument.

Cuvettes, as well as other sample-obtaining and measuring devices, draw their liquid sample into their interiors by vacuum, capillary action, centrifugal force or gravity. While capillary action is quite simple, needing no moving parts, its usefulness is restricted when the materials of the sampling device are hydrophobic, thus precluding capillary action, or have mechanical discontinuities or configurations which create capillary stops, which can impede or halt capillary flow. Other problems can be created when relying on capillary flow; unintended secondary capillary channels along a wall having certain junctions can cause an element of unpredictability to the capillary flow in the main channel. To change the hydrophobic nature of a surface, a wetting agent or surface treatment, such as plasma etching or corona etching, can be applied to the hydrophobic surface to permit capillary action to occur. However, this raises the cost and complexity of the device, and could create contamination of the sample or introduce a deleterious agent into the patient. The problem of capillary stops can be addressed; however, solutions to eliminating capillary stops can require additional parts or very careful manufacturing techniques, both of which increase the cost of the device.

Some devices which use vacuum to draw in the liquid sample have required the use of parts which move relative to one another, such as syringes, or which deflect relative to one another, such as the cuvette shown in U.S. Pat. No. 4,088,448. The requirement for moving parts increases the complexity and cost of the device; devices which have parts which deflect to produce a partial vacuum can lack control as to the size of the change in volume and can be limited in their ability to control the speed of creation of the partial vacuum.

SUMMARY OF THE INVENTION

The present invention is directed to a sample collection and manipulation apparatus and the method for its use. The apparatus uses a thermal pressure chamber to create a partial vacuum or positive pressure to move the liquid sample, typically blood, into a measurement chamber to permit one or more analytes or characteristics of the sample to be measured, typically optically or electrochemically, or by other conventional means. The sample collection apparatus permits component measurements using a small liquid sample volume, allows accurate control over the proportion of the liquid sample to reagent, provides for simplicity of use and accommodates disposability of the sample collection apparatus.

The sample collection apparatus, typically used for collecting a blood sample and measuring a component of the sample with the use of a reagent, includes a receptacle body having a thermal pressure chamber and a sample port. The receptacle body typically includes a body member and a needle cannula extending from the body member, the tip of the needle cannula defining the sample port. Alternatively, the sample port can be created by an opening in the body member. A fluid passageway is formed in the receptacle body and fluidly connects the thermal pressure chamber with the sample port. A measurement chamber is defined along the fluid passageway between the sample port and the thermal pressure chamber.

The air or other gas within the thermal pressure chamber is typically heated to reduce the density of the gas within the thermal pressure chamber prior to taking the sample. The sample port is then placed in contact with the liquid to be sampled, typically by inserting the sharpened tip of the needle cannula into the patient. As the gas within the thermal pressure chamber cools, a partial vacuum is created within the thermal pressure chamber; this draws a liquid sample into the fluid passageway and into measurement chamber. Alternatively, the gas in the thermal pressure chamber can be simply cooled without preheating as the sample port is put in contact with the liquid to be sampled; this also reduces the gas pressure within the thermal pressure chamber. The liquid sample may mix with an analyte detection reagent prior to reaching, within or after reaching the measurement chamber. Appropriate analyte measurement techniques, such as optical, electrochemical, etc., can then be carried out.

Measurements can be carried out using optical measurement techniques, in which case the apparatus functions as a cuvette and defines an optical path intersecting the measurement chamber. If desired, a lens can be an integral part of the optical path formed by the body member of the apparatus.

A primary advantage of the invention is its simplicity. It is simple in construction since there are no moving parts and thus is relatively inexpensive to produce. The proportion of any reagent to the liquid sample size can be quite accurately controlled for accurate and consistent measurements. Since only a very small volume of the liquid sample is needed, small diameter needles can be used to obtain subcutaneous blood samples resulting in very little, if any, pain or discomfort to the patient. This can be especially helpful when a patient is undergoing a regimen of blood work on a regular basis, such as testing for glucose or to monitor the effects of therapeutic drugs.

Another advantage of the invention is that the pressure force created by changing the temperature of the gas in the thermal pressure chamber can be carefully controlled. The volume of the sample displaced is a function of the volume of the thermal pressure chamber and the temperature change within the thermal pressure chamber; therefore either the thermal pressure chamber volume or the temperature change, or both, can be varied to achieve the desired liquid sample size. The rate of temperature change can be controlled to accommodate the desired rate of flow of the liquid sample into or within the receptacle body. The vacuum force created by changing the temperature of the gas within the thermal pressure chamber is typically applied gradually rather than suddenly as can occur with mechanical vacuum producing means. This can provide for a constant pressure profile, or a variety of pressure profiles, as the sample is being drawn into the apparatus; this can be important when the sample is drawn directly from tissue. Extending the time over which the sample may be drawn into the receptacle body helps to ensure that the user has time to position the sample port to be in contact with the sample.

While the gas in the apparatus will often be air, other gases, such as nitrogen, can be used to initially fill the thermal pressure chamber and the fluid passageway. This may be useful when it is desired to exclude oxygen from contaminating the sample liquid, such as when measuring blood oxygen.

The invention is described primarily with reference to a single test run on a liquid sample within a single measurement chamber. However, the invention also contemplates running more than one test on the same liquid sample in the same measurement chamber. The invention is further directed to the use of a set of measurement chambers fluidly coupled to a common sample port to permit a battery of tests to be run using a single liquid sample. The set of measurement chambers could be coupled to separate thermal pressure chambers; some or all of the measurement chambers could be coupled to one or more common thermal pressure chambers.

Other features and advantages will appear from the following description in which the preferred embodiments have been set forth in detail in conjunction with the accompanying drawings.

BRIEF DESCRIPTION OF THE DRAWINGS

FIG. 3 is an exploded perspective view of a second, laminated embodiment of the invention, similar to the apparatus of FIG. 1 but without a needle cannula and with the cover removed;

FIG. 4 illustrates a third, laminated embodiment of the invention, similar to the FIG. 3 embodiment, with a bifurcated thermal pressure chamber used to accommodate a longer needle cannula;

FIG. 5 is a view of a fourth, laminated embodiment similar to that of FIG. 4 but incorporating electrical contacts connected to ion-selective electrodes in the measurement chamber, used for electro-chemical measurements, and a thick film resistor, used to heat the air within the thermal pressure chamber;

DESCRIPTION OF THE PREFERRED EMBODIMENTS

Figure 1:
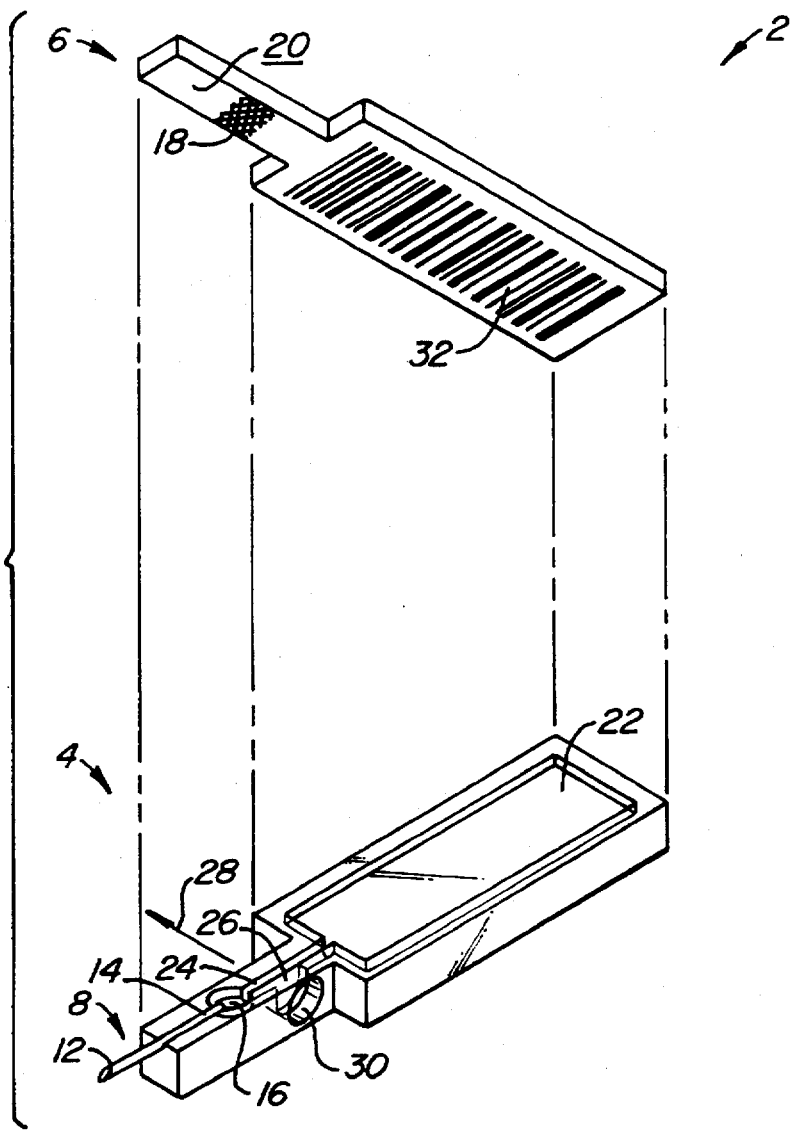
FIG. 1 is an exploded perspective view of an injection molded design of a sample collection apparatus made according to the invention.

FIG. 1 illustrates a sample collection apparatus 2 of an injection molded design. Apparatus 2 includes a base 4 and a cover 6 mountable to and sealable to base 4, typically using adhesive or ultrasonic welding techniques. A needle cannula 8 is insert-molded into base 4 and provides a sample port 10 for apparatus 2 at its sharpened distal end 12. Needle cannula preferably has a cross-sectional lumen area of about 0.0008 $mm^2$ to about 1.8 $mm^2$. Needle cannula 8 is hollow and has a proximal end 14 which opens into a reagent mixing chamber 16 formed in base 4. If desired, the distance from the distal end 12 of needle 8 to base 4 can be chosen to be the depth of penetration of the needle. The reagent 18 for reagent mixing chamber 16 is provided to chamber 16 by being deposited on the inside surface 20 of cover 6. Alternatively, reagent 18 could be applied to surface 20 or placed in reagent mixing chamber 16 by drying a liquid reagent or applying reagent 18 in the form of beads or a powder. Reagent 18 could be a variety of analyte detection reagents, such as enzymes, enzyme substrates, chromogens, immunoassay reagents, chemiluminescent reagents, electroluminescent reagents, redox reagents, kinetic assay reagents including catalytic reagents, and other chemical reagents, or a reagent to aid filtering or other purposes. Chamber 16 is fluidly coupled to a thermal pressure chamber 22 by a relatively narrow slot 24. Slot 24 has an enlarged region 26 which acts as a measurement chamber as will be discussed in more detail below.

Base 4 and cover 6 are both made of transparent, and preferably clear, plastic materials, such as ABS, acrylic or polystyrene. Base 4 and cover 6 are injection molded to provide accurate dimensions, especially along an optical axis 28 defining an optical path passing through measurement chamber 26. This allows appropriate optical measurements to be made on the liquid sample drawn in through sample port 10, combined with reagent 18 in mixing chamber 16 and then drawn into measurement chamber 26. Measurement chamber 26 typically defines a volume of about 0.0002 ml to about 0.1 ml. This embodiment would be appropriate for optically determining analyte concentrations for tests such as glucose or hemoglobin.

A lens 30 is formed in base 4 along optical axis 28 to provide enhanced visualization of the liquid sample in measurement chamber 26. Lens 30 can help to minimize the sensitivity of apparatus 2 to the optical components in the optical measurement meter or other optical measurement device, not shown, used to make the optical measurement.

Surface 20 of cover 6 includes a bar code 32 (which can take any of a variety of forms) placed thereon for two purposes. First, bar code 32 is used to specifically identify the type of reagent 18 and the batch number or calibration factor of the reagent to permit the measurements of the analyte under consideration to be adjusted for particular variances in each batch of reagent 18. Bar code 32 also acts to absorb radiant energy and thus heat the gas, typically air, within thermal pressure chamber 22. Specific methods for heating the gas within chamber 22 will be discussed below with reference to FIGS. 6–9.

Figure 2:
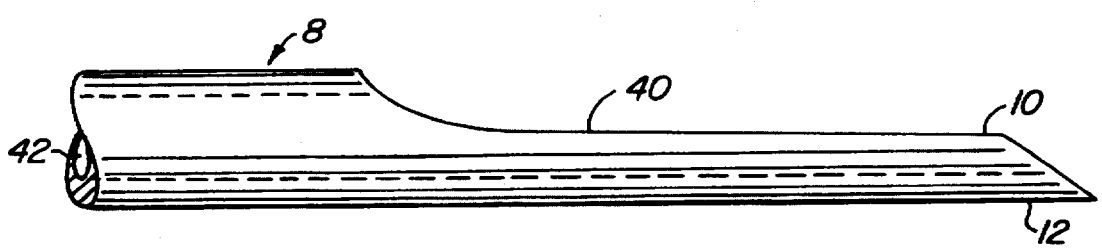
FIG. 2 is an enlarged side view of the distal end of the needle cannula of FIG. 1 showing a cut-out extending from its tip to aid entry of the liquid sample into the needle cannula.

Preliminary tests suggest that needle cannula 8 is preferably a small diameter, about 25–34 gauge, needle about 6 mm long. Needle cannula 8 is preferably made of stainless steel and has an axially extending cut-out 40 at its distal end 12. See FIG. 2. The axial length of cut-out 40 is about 2.5 mm while the radial depth of cut-out 40 is about 50% of the outside diameter of needle 8. Cut-out 40 has been found to be effective in drawing a sample from human tissue by substantially eliminating the possibility of clogging lumen 42 to aid the free flow of the liquid sample.

Apparatus 2 is used by heating the gas within thermal pressure chamber 22 to a set temperature and then, for example, piercing the patient's skin and allowing the gas to cool to draw a liquid blood sample into apparatus 2. The liquid blood sample passes through sample port 10, through bore 42 of needle cannula 8, out proximal end 14 of the needle cannula, and into reagent mixing chamber 16 where it contacts reagent 18. As the gas continues to cool within chamber 22, the liquid blood sample continues to be drawn into apparatus 2 from reagent mixing chamber 16 into slot 24 where a mixture of the blood sample and the reagent pass into measurement chamber 26. The temperature to which the gas within thermal pressure chamber 22 is heated and the size of the thermal pressure chamber are chosen so that the liquid blood sample which is drawn into apparatus 2 is sufficient to effectively fill measurement chamber 26 but preferably does not cause the liquid blood sample to be drawn into thermal pressure chamber 22. By using a very small diameter needle cannula 8 and small volumes for mixing chamber 16 and slot 24, the volume of the liquid blood sample can be quite small.

One of the advantages of the invention is that it minimizes the volume of the liquid sample used. This liquid sample volume can be further minimized by the following technique. After the sample has been mixed with the reagent and has been moved to measurement chamber 26, the only volume that matters at that point is the volume of the liquid sample in measurement chamber 26. Any other sample remaining in mixing chamber 16 or slot 24 serves no purpose and is thus just excess. By drawing only enough of the liquid sample equal to the volume of measurement chamber 26, the user can then withdraw the sample port from the sample, agitate the sample if desired in the mixing chamber by thermal cycling of thermal pressure chamber 22 so that the liquid sample mixes with the reagent, and then move the sample liquid within the mixing chamber into measurement chamber 26 (thus drawing air through sample port 10). To ensure that enough sample has been obtained, fluid sample presence at a specific point in the flow path can be monitored; this can be done manually by a user or automatically by a suitable instrument. The fluid movement of the liquid sample can be controlled by precise control of the rate and amount of temperature drop in thermal pressure chamber 22. The total volume of the liquid sample required would be substantially less than the total volume of bore 42, slot 24 (which includes measurement chamber 26) and mixing chamber 16 combined.

Digressing for a moment, considerations behind the design of thermal pressure chamber 22 will be discussed. Chamber 22 must enclose a specific volume of air, or other gas, and allow that air to be quickly heated and cooled. The aim is to initially heat the air to expel some of the air out of apparatus 2 through sample port 10 into the ambient environment. Sample port 10 is then placed in communication with the liquid sample, typically subcutaneously; heated air within thermal pressure chamber 22 is then cooled so that the contracting air draws the liquid sample into apparatus 2.

The physics of the system can be described through the gas equation pV=nRT, where p is the air pressure, V is the volume of gas, n is the number of moles of the gas, R is the universal gas constant and T is the temperature of the air in absolute degrees, for example degrees Kelvin. The air temperature in apparatus 2 is first raised to the temperature $T_H$, with the air allowed to expand and be expelled from apparatus 2. The air in apparatus 2 is then allowed to cool while sample port 10 is in communication with, for example, the blood sample, during which time the temperature drops by $\Delta T$ to the low temperature $T_L$. The change in air volume when the temperature drops should be equal to the amount of sample to be drawn into apparatus 2, which includes, for instance, the total volume within needle cannula 8, mixing chamber 16 and slot 24. Thus, the total air volume at the start of the cooling phase drops by $\Delta V$ to the final volume of $V_{TPC}$. The air pressure at the higher temperature starts at atmospheric pressure, $P_{ATM}$, and ends at a value that is different from atmospheric by $\Delta P$. This ending pressure is necessary to balance any other pressures on the sample, such as surface tension forces of the sample in apparatus 2, and may be above or below atmospheric.

There are two equations of state that can be written, corresponding to the two conditions of the high and low temperature.

High temperature: $P_{ATM} V_T = nRT_H$.

Low temperature: $(P_{ATM} + \Delta P) V_{TPC} = nRT_L$

Recognizing that $V_T = (V_{TPC} + \Delta V)$ and $T_H = T_L + \Delta T$, the two equations of state may be combined into one equation that must be satisfied.

$$\frac{\Delta V}{V_{TPC}} = \frac{\Delta T}{T_L} + \frac{\Delta P}{P_{ATM}} + \frac{\Delta T \Delta P}{T_L P_{ATM}}$$

For the small $\Delta T$ values to be used here, this reduces to:

$$\frac{\Delta V}{V_{TPC}} \approx \frac{\Delta T}{T_L} + \frac{\Delta P}{P_{ATM}}$$

This equation can be used to find $V_{TPC}$, the volume required in the thermal pressure chamber 22 in the following example.

The change in temperature is the difference between the temperature to which the gas in apparatus 2 is heated before drawing the sample, and the subsequent temperature to which it is cooled while drawing the sample. The initial heating temperature is limited by such constraints as the stability of the materials with temperature, the power available for heating and the time available for heating. An initial temperature of 50° C. is reasonable. The ending temperature depends on the method of removing heat and the ambient temperature. If the ambient temperature is 25° C. and an exponential drop in temperature due to convection to ambient is assumed, then halting the temperature drop once it reaches 30° C. will give a well-defined end point that is 20° C. lower than the initial temperature. The equation requires the use of degrees Kelvin, so in this scenario, $\Delta T = 20°$ K. and $T_L = 303°$ K.

Typical values for the volumes of bore 42 in needle cannula 8, measurement chamber 26 and associated connecting passages are 0.2 µl, 0.2 µl, and 0.3 µl, respectively, totalling 0.7 µl. If it is desired to fill this entire volume with sample, then $\Delta V = 0.7$ µl. If a smaller volume is needed, then a corresponding smaller $\Delta V$ value is appropriate.

If the surface of the fluid passages is hydrophobic, and the average cross-sectional dimensions of the passage are 0.025 by 0.025 cm, then a typical value for the capillary force acting on this 0.000625 $cm^2$ of fluid is −2 dyn. The negative force indicates that an additional force from the thermal pressure chamber 22 is required to pull the sample into the fluid passage since it is hydrophobic. Thus, $\Delta P = -3,200$ dyn/cm$^2$. Atmospheric pressure $P_{ATM}=1\times10^6$ dyn/cm$^2$. Using, in this example, the above equations shows that $V_{TPC}$ must be 16 times $\Delta V$ or 11.2 µl to draw a 0.7 µl sample.

The shape of chamber 22 will usually be chosen to maximize the rate of warm-up and cool-down of the enclosed air or other gas. This typically calls for a large surface area-to-volume ratio, that is providing a wide, flat chamber. The thermal mass of the chamber walls should be as low as possible to minimize delay in heating or cooling, unless the thermal mass of base 4 and cover 6 are to be used to cool the gas within thermal pressure chamber 22 after having been heated with radiant energy.

FIG. 3 illustrates an alternative embodiment of the invention of FIG. 1 in which the parts are laminated instead of being injected molded. However, corresponding parts are referred to with corresponding reference numerals and will not be discussed except where they differ. Apparatus 2a has a sample port 10a defined by a blunt extension 44 of base 4a instead of a sharpened needle cannula as in FIG. 1. Apparatus 2a is thus used for sample collection and measurement when the liquid sample is obtainable as a surface sample, such as on the skin of a user or within a dish or other container. Another difference between apparatus 2 of FIG. 1 and apparatus 2a of FIG. 3 is the elimination of a separate reagent mixing chamber 16. Reagent 18, if used with apparatus 2a, can be applied along slot 24a between measurement chamber 26a and sample port 10a, or at measurement chamber 26a, or after the measurement chamber. Base 4a is preferably a two-layer member with the outer layer 46 being made of clear Mylar, ABS sheet or other similar materials. Middle layer 48 could be a preformed or stamped plastic layer, with or without adhesive layers, which would define the lateral extent of thermal pressure chamber 22a and slot 24a (including measurement chamber 26a). Cover 6a, like outer layer 46, can be made of clear Mylar, ABS sheet, etc. An advantage of this design is that it can be made by an inexpensive continuous fabrication process. Another advantage of this laminated apparatus 2a is that its flat design gives a large surface-to-volume ratio in pressure chamber 22a for fast heating and cooling of the gas within the pressure chamber. Since the optical axis 28a defines an optical path length which is not well defined, typically due to adhesive layer thickness variability, this embodiment is useful for measurements in which the optical length is not critical, such as in some coagulation assays. If desired, a two zone heating regimen could be used. That is, the temperature in measurement chamber 26a could be set at a constant temperature, such as 37° C., while the thermal pressure chamber 22a could be heated separately. Also, the rate and degree of cooling of the air in thermal pressure chamber 22a could be controlled to actively control sample flow.

FIG. 4 illustrates a sample collection apparatus 2b similar in construction to apparatus 2a but having an integral needle cannula 8 and a bifurcated pressure chamber 22b. The cover for apparatus 2b is not shown for clarity. Needle cannula 8 can be held in place by an adhesive or through other methods. The extra length of needle cannula 8 permits a greater surface area for bonding to, and thus an enhanced seal with, base 46 and its cover (not shown). If desired, the distance from the distal end 12 of needle 8 to base 4b can be chosen to be the depth of penetration of the needle.

FIG. 5 shows another embodiment, also without its cover. Apparatus 2c is similar to apparatus 2b but has an extra length outer layer 46c to which terminals 50 are mounted. Terminals 50 connect to ion-selective electrodes 52 placed within measurement chamber 26c and to a thick film resistor 54 formed along the surface of thermal pressure chamber 22c. This permits thick film resistor 54 to be used to heat the gas within thermal pressure chamber 22c for rapid and precise control of the temperature of a gas within the chamber. During manufacturing, thick film resistor 54 could be laser-trimmed to also carry calibration information for ion-selective electrodes 52. Thus, a meter coupled to terminals 50 could be used to measure the resistance of resistor 54 to obtain calibration information for ion-selective electrodes 52; a current could then be applied through resistor 54 for a chosen time and a chosen current level based on the measured resistance to dissipate a known power in the resistor and thus precisely heat the gas within pressure chamber 22c. Apparatus 2c would be suitable for any electrochemical assay, such as glucose, electrolytes such as potassium or sodium, or blood gasses.

Figure 6:
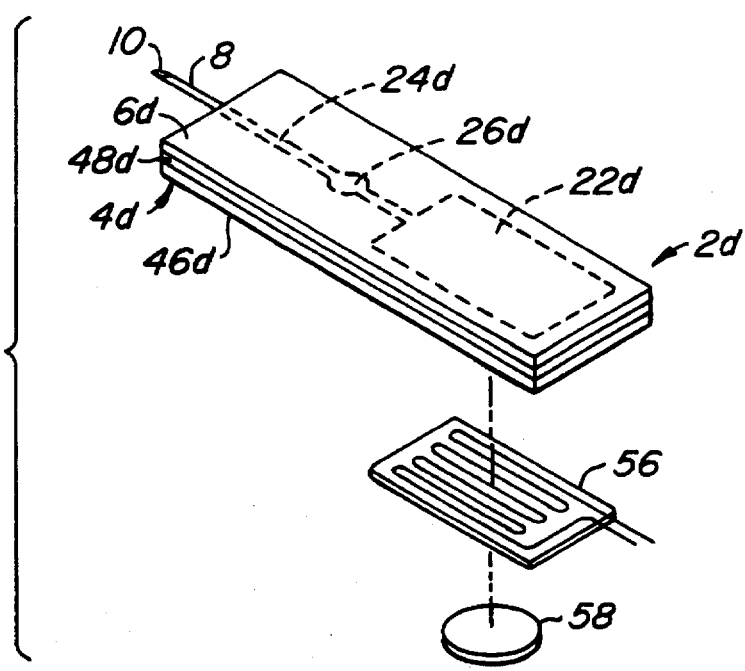
FIG. 6 is a simplified view showing a typical sample collection apparatus made according to the invention together with a direct contact heater and a temperature sensor in an exploded relationship.

FIG. 6 illustrates a typical sample collection apparatus 2d together with a direct contact heater 56 and a temperature sensor 58. Heater 56 is preferably a Kapton heating element with a serpentine resistance wire which is used in direct contact on one or both sides of sample collection apparatus 2d. Temperature sensor 58 can be used if desired but may not be necessary. Direct contact heater 56 provides moderately fast response time, primarily depending on the amount of power supplied to it. Cool-down time depends on the thermal mass of base 4 and cover 6 as well as temperature loss to the ambient environment; cool-down time is thus sensitive to ambient conditions, such as airflow speed past apparatus 2d. This is a relatively inexpensive method of heating apparatus 2d. The use of temperature sensor 58 permits feedback to control the temperature of heater 56. Instead of resistive heating element 56, a positive temperature coefficient thermistor (not shown), which automatically heats to a set temperature, can be used; this element is a simple and low-cost heating element but has a relatively slow warm-up time since it cannot be initially set to a high temperature to boost the initial heat output.

Figure 7:
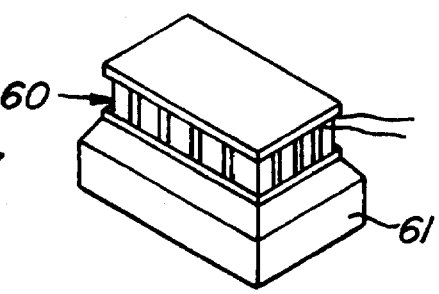
FIG. 7 shows a Peltier device which can be used to heat and cool the thermal pressure chamber.

Instead of merely heating device 2d with one or more direct contact heaters 56, device 2d could be both heated and cooled with a Peltier device 60 as shown in FIG. 7. Peltier device 60 provides both heating and cooling, as is conventional, by merely changing the direction of current flow through the device and use of a heat sink 61 as a part of the device. While cooling can be adjusted, can be relatively quick and has the advantage of being independent of ambient conditions, rapid cooling is relatively inefficient. Therefore, this method of heating and cooling can be relatively expensive and power consuming. One distinct advantage of employing a device that can actively provide cooling is that the thermal pressure chamber pre-heat time, that is the time before the sample port can be brought into contact with the sample, can be eliminated. The gas can be cooled below ambient to provide the partial vacuum, so the sample collection device is instantly available for use.

Figure 8:
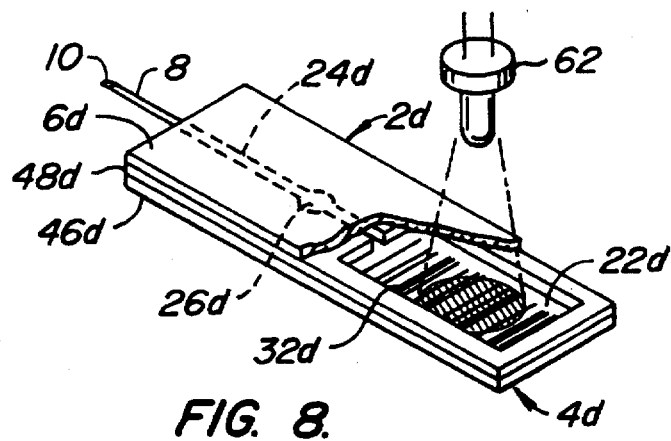
FIG. 8 schematically illustrates the use of a radiant energy heat source to heat the thermal pressure chamber of the sample collection apparatus of FIG. 6.

FIG. 8 illustrates a radiant energy heat source 62 used to direct radiant energy onto an internal absorptive surface, such as bar code 32d, lining the thermal pressure chamber 22d of apparatus 2d. This noncontact method is very repeatable since it does not rely on intimate surface contact between the heating element and apparatus 2d as do the embodiments of FIGS. 6 and 7. Since bar code 32d, or other radiant energy absorptive surface, lines the inside wall of pressure chamber 22d, the gas within the pressure chamber warms up very quickly, typically within one second. While this method of heating the gas within the pressure chamber does not lend itself to feedback control, different temperatures can be easily provided by changing the length of time of the application of heat source 62 or the intensity of the radiant energy emanating from heat source 62 and/or received by chamber 22d. This method of heating the gas within pressure chamber 22d is quite simple and low cost. It also lends itself to cooling chamber 22d by using the thermal mass of base 4d and cover 6d as a heat sink to cool the gas within chamber 22d.

Figure 9:
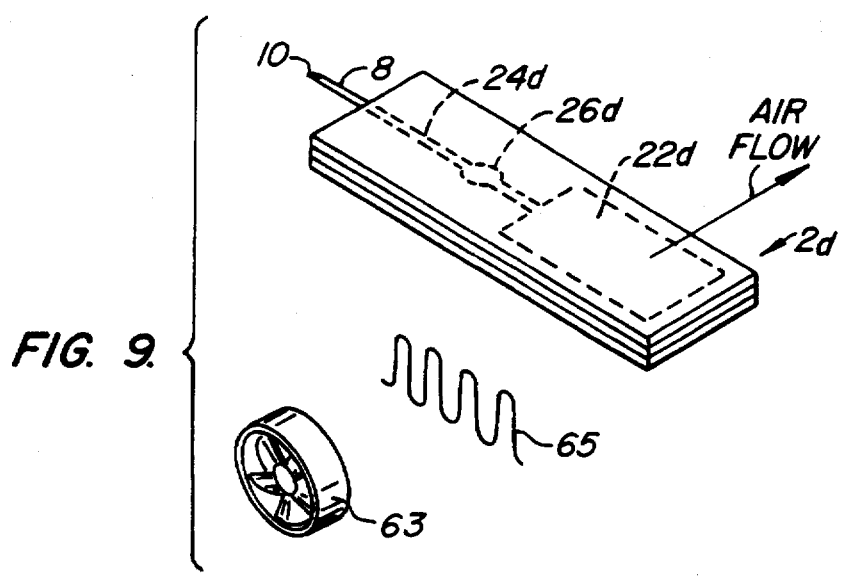
FIG. 9 illustrates the forced convection heating of the sample collection apparatus of FIG. 6.

FIG. 9 illustrates a further method of heating or heating and cooling of the gas within pressure chamber 22d of apparatus 2d. This method uses forced convection using a fan 63 which blows air across a low mass heater 65 to relatively quickly heat the air within thermal pressure chamber 22d. Once sample port 10 is in position, heater 65 can be turned off so that the air flow past apparatus 2d quickly becomes ambient temperature to provide relatively rapid cooling of apparatus 2d. While this provides a noncontact method for both heating and cooling, fan 63 and heater 65 are relatively bulky and expensive.

Figure 10:
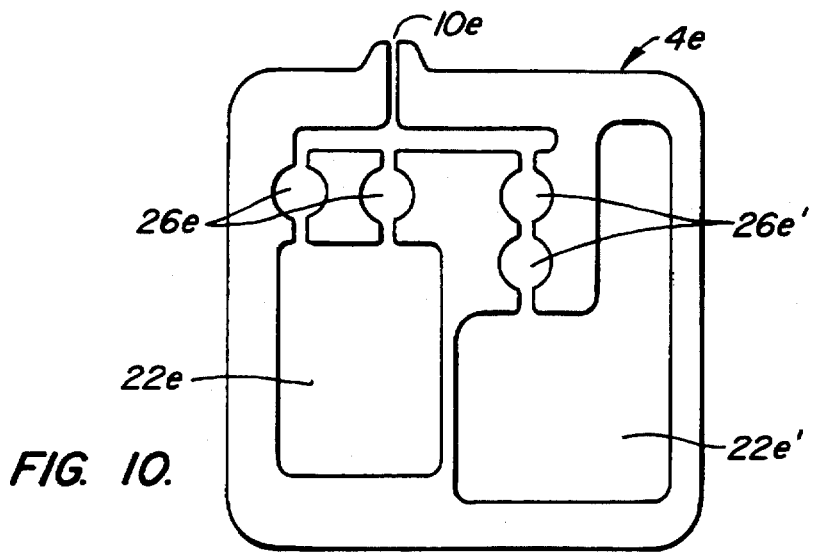
FIG. 10 illustrates in simplified form a sample collection apparatus including two thermal pressure chambers, each thermal pressure chamber having a pair of measurement chambers associated therewith, the two measurement chambers opening into one of the thermal pressure chambers being in parallel while the two measurement chambers connected to the other thermal pressure chamber are in series.

FIG. 10 is a schematic view of a modification of the base of the apparatus of FIG. 3. Base 4e shows a pair of thermal pressure chambers 22e and 22e'. Pressure chamber 22e is fluidly coupled to sample port 10e through a pair of measurement chambers 26e arranged parallel to one another. This permits a different reagent 18 to be used for each of chambers 26e as desired. Thermal pressure chamber 22e' has a pair of measurement chambers 26e' arranged in series to accommodate stepwise mixing of two different reagents or to simply enhance the mixing of a reagent with the liquid sample as the liquid sample passes through measurement chambers 26e'. series connected measurement chambers permit sequential measurement of different constituents in the same sample when different measurement sensors are used in the connected chambers or within one chamber. This can have particular advantage in some applications, such as neo-natal blood gas monitoring, where minimizing sample volume is critical and a single small sample can be moved from one sensor to the next. Thermal pressure chambers 22e and 22e' could be heated to the same temperature, they could be heated to different temperatures, they could be cooled at different rates or they could be cooled to two different temperatures.

Figure 11A:
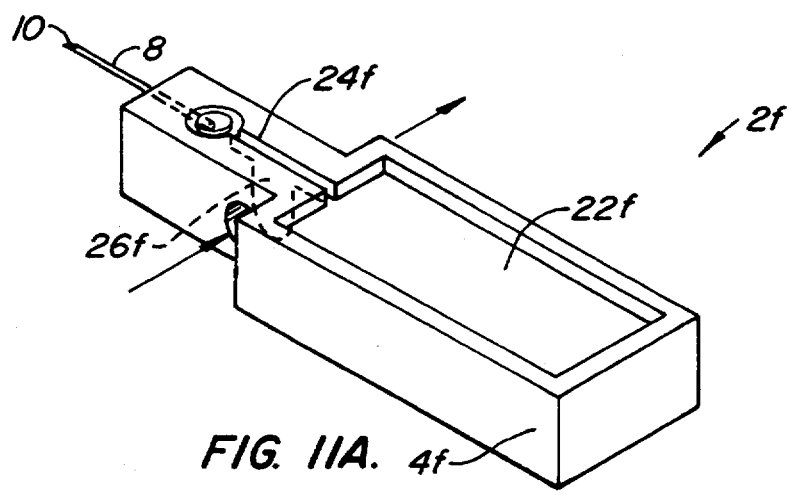
FIGS. 11A–11C illustrate a further embodiment of the invention, similar to the FIG. 1 embodiment, including a reagent-containing filter between the sample port and the measurement chamber.
Figure 11B:
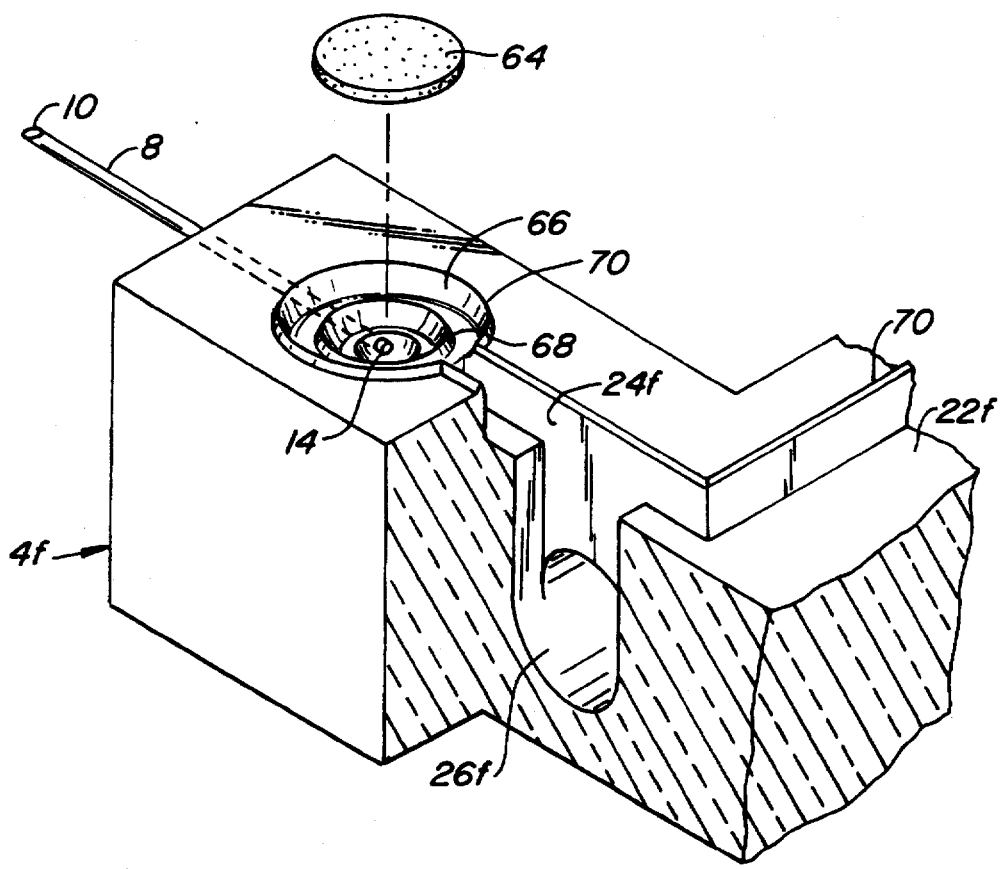
Figure 11C:
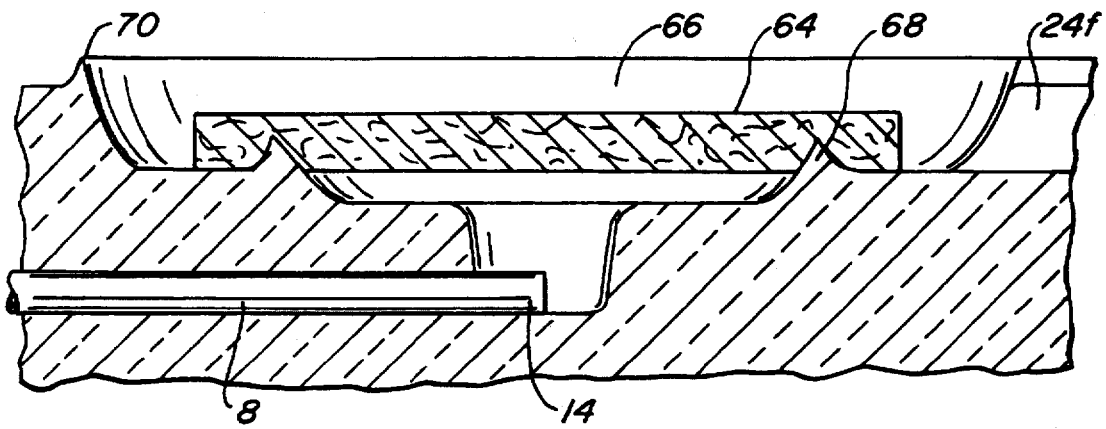

FIGS. 11A–11C illustrate a further alternative embodiment of the invention in which sample collection apparatus 2f adds a filter 64 upstream of measurement chamber 26f. Apparatus 2f is most similar to apparatus 2 shown in FIG. 1 with the addition of filter 64 positioned directly above the proximal end 14 of needle cannula 8. Filter 64 is positioned within a filter region or well 66. Filter 64 is preferably of polyethylene and is ultrasonically welded in place through the use of a raised rim 68 which acts as an energy director for the ultrasonic welding. The ultrasonic tip of the welder can simultaneously cut and weld the filter from a long strip of filter stock in a continuous on-line process. The cover, not shown, is ultrasonically welded in place, as is conventional, using a second raised rim 70 as an energy director to help seal region 66, slot 24f and chamber 22f.

Filter 64 can be used as a substrate for chemical reagents that are needed to perform the assay. The large surface area of filter 64 touching the liquid sample provides an effective way to mix the reagent with the sample. Filter 64 also can be used to contain antibodies that will agglutinate or bind red blood cells together as a method of increasing its effectiveness at filtering. With devices which use capillary forces to pull blood into a sample device, there is a strong tendency for red cells to bypass the filter and work around its edge where the filter meets the body due to the use of hydrophilic filter and plastic body parts with these capillary force devices. However, in the present invention, the base cover and filter may be hydrophobic so that the sample liquid stays in place until drawn into apparatus 2f and through filter 64 by the partial vacuum within thermal pressure chamber 22f; bypass wicking need not be a problem with the present invention.

Filter 64 could also be welded into place at the same time as the cover, using just one set of energy directors for the melt. This would work for a plastic filter material that is easily weldable. Glass filter material cannot be welded, but could be held in a compression fit with the cover providing the necessary compression. Another alternative is a molded filter that would be dropped into a hole in the body, and then held in compression by the cover.

Figure 12:
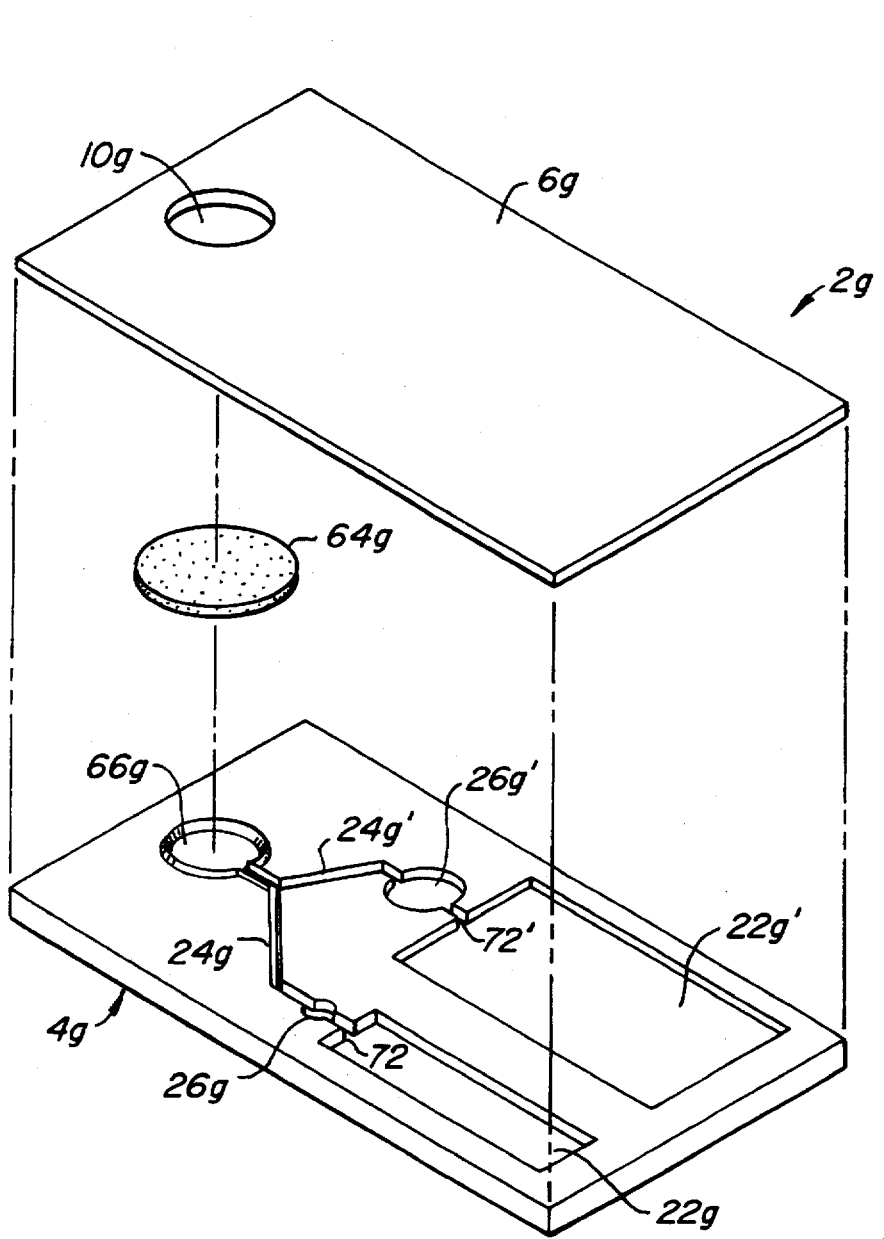
FIG. 12 illustrates an embodiment of the invention similar to the embodiments of FIGS. 10 and 11A–11C.

FIG. 12 illustrates a further embodiment of the invention similar to the embodiments of FIGS. 10 and 11A–11C. Apparatus 2g includes a cover 6g having a sample port 10g positioned to overlie a filter region 66g formed in body 4g with a filter 64g captured therebetween. A liquid sample can be applied to filter 64g through port 10g using, for example, a pipette, a drop of blood from a finger stick, or any other suitable means. The liquid sample is then drawn into measurement chambers 26g, 26g' as the gas within chambers 22g, 22g' cools.

It is often desirable to ensure that the liquid sample not enter the thermal pressure chambers. This can be aided by using stop junctions, such as stop junctions 72, 72' at the junctions of slots 24g, 24g' and thermal pressure chambers 22g, 22g'. The stop junctions are configured to permit gas to pass relatively freely but to substantially prevent the passage of liquids.

Fluid passages in the above embodiments could be configured with partial obstructions to aid mixing reagent 18 with the liquid sample. The sample within the collection apparatus could also be agitated to aid mixing. This agitation could be done mechanically or thermally; thermal cycling of the thermal pressure chamber, that is raising and lowering of the temperature of the gas within the thermal pressure chamber, will create back and forth movement of the liquid sample for agitation and enhanced mixing. Agitation of the liquid sample by thermal cycling of the thermal pressure chamber could also be used to determine viscosity changes or to measure viscosity of the liquid sample.

Nothing in the previous description should imply that the presence of a measurement chamber is required in the invention. The invention is also applicable to a device that provides a convenient means to sample and manipulate blood, to be then passed to another device, not described here, for possible measurement.

The embodiments of the invention that have been described have typically used plastic materials for the receptacle body. It is envisioned that other materials and fabrication processes can be used to produce other embodiments of the invention. For example, materials and processes commonly used for microelectronic devices, such as ceramic and silicon substrates and thick film, thin film and micromachined structures, are other means of implementing this invention in devices that are much smaller than have been otherwise described.

Other modifications and variations can be made to the disclosed embodiments without departing from the subject of the invention as defined in the following claims. For example, the base and cover could be made by other manufacturing techniques, such as blow molding. When electrodes are used for measurement, the electrodes could be potentiometric, ampereometric or conductometric electrodes, such as cationic electrodes, pH measuring electrodes, anionic electrodes or polarographic electrodes, in addition to ion-selective electrodes 52. The invention has been described primarily with reference to measuring properties of blood; the invention could be used for other applications as well.

What is claimed is:

1. A method for collecting a liquid sample, said method comprising:

contacting a sample port of a receptacle body with the liquid sample, the sample port opening to the ambient atmosphere, the sample port coupled to a thermal pressure chamber by a fluid passageway;

cooling the gas within the thermal pressure chamber thereby drawing a liquid sample into the receptacle body by a partial vacuum created by said cooling of the gas; and raising and lowering the temperature of the gas within the thermal pressure chamber to move the liquid sample within the receptacle body.

2. The method of claim 1 wherein the temperature raising and lowering step is carried out by controllably raising and lowering the temperature of said gas.

3. The method of claim 1 wherein the temperature raising and lowering step is carried out to agitate the liquid sample within the receptacle body.

* * * * *